(12) United States Patent
Etter et al.

(10) Patent No.: US 7,655,351 B2
(45) Date of Patent: Feb. 2, 2010

(54) ADMINISTERING DEVICE WITH A POWER SOURCE CONTACTED BY SPRING FORCE

(75) Inventors: Philip Etter, Ittigen (CH); Marco De Polo, San Mateo, CA (US); Remo Steiner, Muenchenbuchsee (CH)

(73) Assignee: Disetronic Licensing AG, Burgdorf (CH)

( * ) Notice: Subject to any disclaimer, the term of this patent is extended or adjusted under 35 U.S.C. 154(b) by 814 days.

(21) Appl. No.: 11/345,640

(22) Filed: Feb. 1, 2006

(65) Prior Publication Data

US 2007/0178776 A1 Aug. 2, 2007

(51) Int. Cl.
  *H01M 2/10* (2006.01)
(52) U.S. Cl. .................................... 429/100; 439/840
(58) Field of Classification Search ........... 429/96–100; 439/840, 500
  See application file for complete search history.

(56) References Cited

U.S. PATENT DOCUMENTS

| | | | | |
|---|---|---|---|---|
| 3,881,961 A * | 5/1975 | Nation | ........................ | 429/97 |
| 4,083,011 A | 4/1978 | Ferrell et al. | | |
| 4,576,211 A | 3/1986 | Valentini et al. | | |
| 5,384,207 A * | 1/1995 | Ohtani | ........................ | 429/100 |
| 6,007,941 A * | 12/1999 | Hermann et al. | ............... | 429/99 |
| 6,037,078 A * | 3/2000 | Siu-Man | ........................ | 429/96 |
| 6,338,914 B1 * | 1/2002 | Schuurmans | ................. | 429/97 |
| 6,549,423 B1 * | 4/2003 | Brodnick | ...................... | 429/99 |
| 6,565,395 B1 * | 5/2003 | Schwarz | ...................... | 439/840 |
| 7,390,214 B2 * | 6/2008 | Tsiang | ........................ | 429/100 |
| 7,458,862 B2 * | 12/2008 | Zhao et al. | ................... | 439/840 |
| 2004/0018420 A1 | 1/2004 | Nakajima et al. | | |

FOREIGN PATENT DOCUMENTS

| | | |
|---|---|---|
| EP | 0 493 079 A2 | 7/1992 |
| EP | 0 493 079 A3 | 7/1992 |
| WO | WO 82/03254 A1 | 9/1982 |
| WO | WO 98/47552 | 10/1998 |

* cited by examiner

*Primary Examiner*—Briggitte R Hammond
(74) *Attorney, Agent, or Firm*—Dorsey & Whitney LLP

(57) ABSTRACT

Administering device for infusing or injecting a product, comprising a housing (1, 2) with a receiver (3) for the product, a compartment (7) for a power source in order to supply the conveying mechanism (4) with electrical energy, a first contact spring (15) which is disposed in the compartment and places a terminal of the power source in an electrically conducting contact by means of a spring force when the power source is disposed in the compartment (7), and a second contact spring (16) for establishing an electrically conducting contact for an opposite terminal of the power source, likewise by means of spring force.

18 Claims, 4 Drawing Sheets

ADMINISTERING DEVICE WITH A POWER SOURCE CONTACTED BY SPRING FORCE

The invention relates to the connection of the power source of a device for administering an infusion or injection, comprising two resilient spring contacts.

These days, administering devices for infusions or injections, e.g. insulin pumps, are usually carried on the body by the user. This makes it necessary for the device to incorporate its own power source, a battery or an accumulator, which is accommodated in a compartment of the device as a rule. This being the case, the positive terminal of the battery cell, for example, is connected to a contact permanently attached to the cell, whereas the negative terminal is placed against a contact in the form of a helical spring, for example. Since the device is exposed to considerable mechanical forces during day to day use and the individual parts have different moments of inertia due to their specific weights, a situation may arise where some force acting on the device, caused by the user jumping for example, causes the battery to be so far inwardly biased for a brief moment that the positive terminal becomes separated from the contact, thereby causing the device to be reset. However, this must be avoided at all costs because an undesirable and often unnoticed re-setting of the device can have implications with respect to the dispensing of the product, thus placing the health of the user at risk.

The objective of the invention is to ensure a reliable connection between the power source and the down contacts co-operating with the terminals in every situation in which the administering device might be subjected to stress.

The administering device to which the invention relates has a compartment for accommodating a power source, e.g. a battery, an accumulator or a fuel cell, to supply a conveying mechanism with electrical energy. The compartment is a constituent part of the device and has a cover, by means of which the access opening of the compartment on the housing can be closed, rendering it watertight. As a rule, this is a screw-on cap, which may be provided with a sealing ring to prevent penetration by water.

In order to connect the power source lying in the compartment with a consumer, e.g. the driver mechanism, a contact is provided for each terminal, which is connected to down conductors, either directly or via conducting connections mounted in the compartment interior, e.g. wires or metal tapes. These down conductors are run through the wall of the compartment, e.g. on its surface, to the exterior, i.e. through into the device. The down conductors are preferably embedded in the wall by moulding, in the region of the passage through the wall of the compartment, which enables them to be run safely through the wall, keeping them sealed and protecting them from damage. It is likewise conceivable for the down conductors to be embedded either partially or entirely in the wall of the compartment by moulding, in which case only the terminals project out from the wall.

The contacts to the terminals of the power source are provided in the form of contact springs, preferably compression springs, which means that the contacts possess a pre-defined amount of spring force due to their shape and their material. Consequently, in the event of movements of the power source caused by shaking, impact or vibration, for example, they can follow this movement away from the contact, so that the contact of the terminal of the power source does not migrate relative to the contact spring. Any appropriate spring of any type may be used as the contact spring, e.g. leaf springs, helical springs, coil springs, bent springs, to name but a few. What is important is that the springs have a spring path that is big enough to compensate for more than the maximum possible deflection of the power source.

All the contact springs may be disposed in the interior of the compartment or partially in the compartment and may be disposed on the cover or exclusively in the cover. In a preferred embodiment, a first contact spring is disposed in the interior of the compartment and a second contact spring is disposed on the cover. In this case, the power circuit between the power source and consumer is not established until the cover is placed on the housing to close it and the second contact spring in the interior of the cover is therefore in contact with the terminal or opposite terminal of the power source. In order to transmit power, the second contact spring may itself be an electrical down conductor or may be conductingly connected to a down conductor. However, the second contact spring is preferably in contact with a down conductor via a connecting element.

To this end, the cover has a connecting element on the side which is screwed into the compartment. This connecting element is permanently connected to the cover. This permanent connection may be provided in the form of a form fit or a bonded or welded connection, for example. The connecting part is made from a conductive material and has at least one extension, which extends parallel with the side walls of the compartment. Instead of one extension, the connecting part might have several extensions or be provided in the form of a ring. Several extensions are preferably provided on the connecting part, disposed in the peripheral direction and spaced at uniform distances apart from one another. One or more radial projections may be provided on the extension or extensions. These projections may be formed in the conducting material by punching, for example. The extensions are also biased by a radial pre-tensioning, preferably a pre-tensioning directed radially outwards.

When the cover is screwed on, the extension/extensions or the ring establish/es a contact with the electrical down conductor running in the interior of the compartment. The projections and said pre-tensioning mentioned above are used as a means of establishing a reliable contact. The down conductor may be of any shape that will guarantee a reliable contact. For example, if there were only one extension on the connecting element, it would be necessary to provide a down conductor with the shape of a circle in order to guarantee a reliable contact. If the extension itself is provided in the form of a ring, a narrow circle segment will suffice as a down conductor contact.

In order to prevent a flow of current if the power source is incorrectly inserted, one of the contact springs is provided with a mispoling protector in a preferred embodiment. It is particularly preferable if the contact spring disposed on the cover is provided with this mispoling protector. The mispoling protector is made from a non-conducting material. It may be of any shape, although it is essentially in the shape of a ring by preference and even more preferably is provided in the form of an annular disc. The mispoling protector has a thickness which enables it to place a terminal or opposite terminal standing proud of the power source in contact with the contact spring, whereas the opposite terminal or mispoling which does not stand proud is not able to come into contact with the contact spring. The mispoling protector is preferably attached directly to the contact spring, e.g. adhered to it.

Advantageous features and combinations of features are also described in the dependent claims. The features described above and those defined in the dependent claims and their combinations are mutually complementary and interchangeable.

An example of an embodiment of the invention will be explained below with reference to the appended drawings. Features which become apparent from the embodiment described as an example advantageously supplement the subject matter of the claims, each individually and in every combination of features, as do the embodiments described above. Of the drawings:

Figure 1:
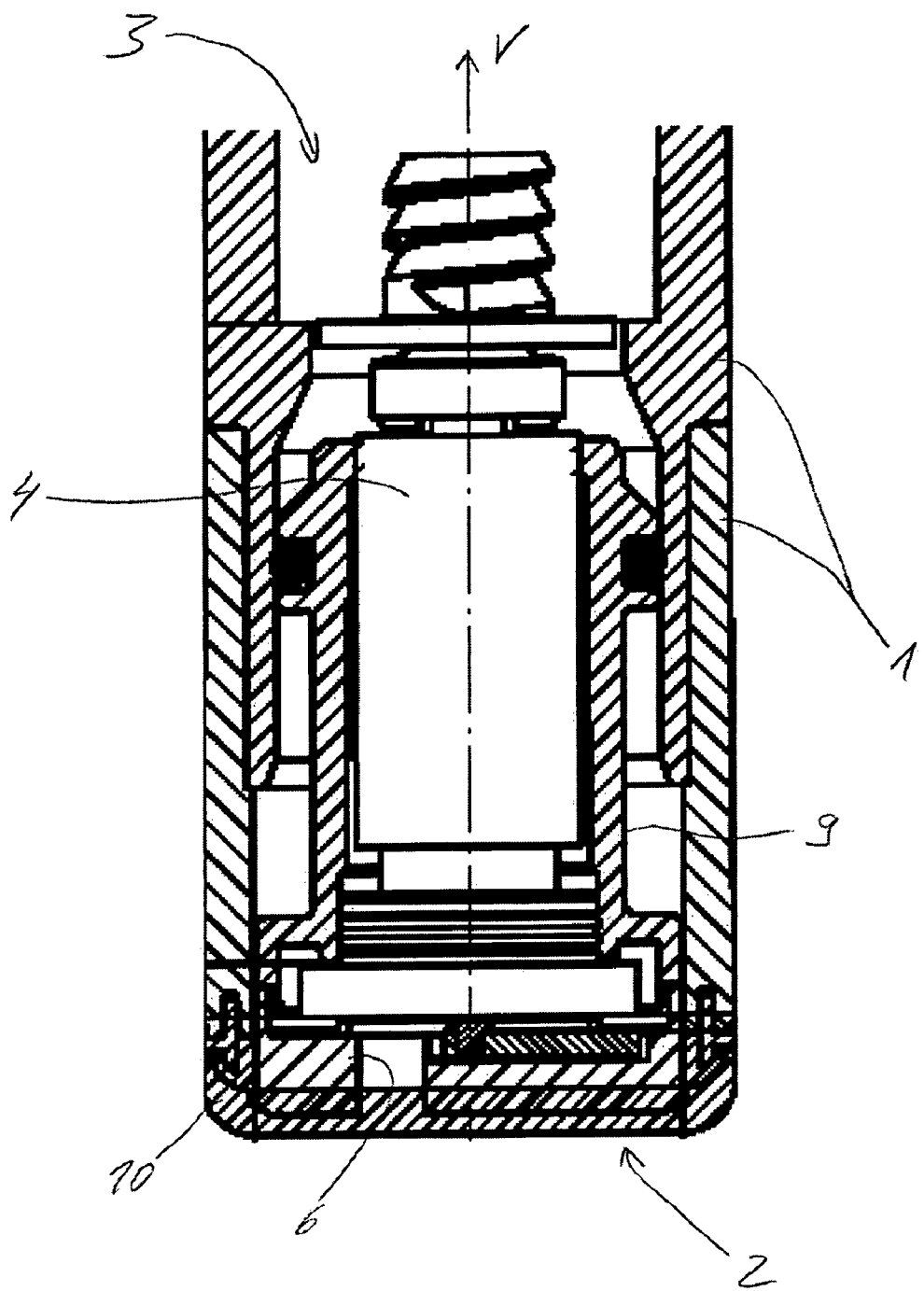
FIG. 1 is a longitudinal section showing part of an administering device.

FIG. 1 is a longitudinal section illustrating a part of an administering device. The administering device is an infusion device for infusing insulin, for example. The infusion device is compact and lightweight so that it can easily be carried in or under the clothing. Apart from the characterising features proposed by the invention, the infusion device may correspond to standard infusion devices used for self-administration, for example insulin pumps.

The infusion device has a housing comprising a first housing shell 1 and a second housing shell 2, which, in the joined state illustrated, form a watertight case for moisture-sensitive components of the infusion device. Housing shell 1 specifically forms a receiver 3 for a product container, which is preferably an ampoule, filled with a product to be administered, for example insulin, of the type used for the treatment of diabetes or other treatments where the patient administers the relevant drug himself. In FIG. 1, the receiver 3 is empty, i.e. there is no product container inserted. The first housing shell 1 also encloses a driver mechanism 4, by means of which the product can be conveyed out of the product container. In particular, the driver mechanism 4 may be a plunger driver with a plunger which can be moved in the product container in a forward drive direction V and a drive mechanism for driving the plunger forward.

The housing shell 1 forms the side wall of the housing 1, 2, but is open at a bottom end face across its entire internal cross-section. The components to be disposed in the housing 1, 2, in particular the driver mechanism 4, can be introduced into the housing shell 1 through the resultant opening and fitted during assembly of the infusion device. Housing shell 2 closes the terminal opening of housing shell 1 in a watertight arrangement and in the connected state forms the base of the housing 1, 2.

The housing shell 2 comprises several parts, although the several parts are connected to one another to form a solid unit. Housing shell 2 comprises a dimensionally stable support structure 6 and a seal 10, which form the base of the housing 1, 2, and a holder 9 projecting from the support structure 6 into the housing shell 1 for the for the driver mechanism 4. The support structure 6 and the holder 9 are formed from the same dimensionally stable, curable plastic material. The seal 10 is injection-moulded onto the support structure 6. The seal 10 is made from a thermoplastic elastomer. The support structure 6 and the seal 10 are joined to one another in a form fit and by a material join. The support structure 6 and the holder 9 are joined to one another in a form fit and a non-positive fit. The support structure 6 is formed by an injection moulding process and the seal 10 is injected around it. Accordingly, due to the multi-component injection mould process, a particularly solid joint is obtained between the support structure 6, which constitutes a hard component, and the seal 10 in the form of a soft component.

Figure 2:
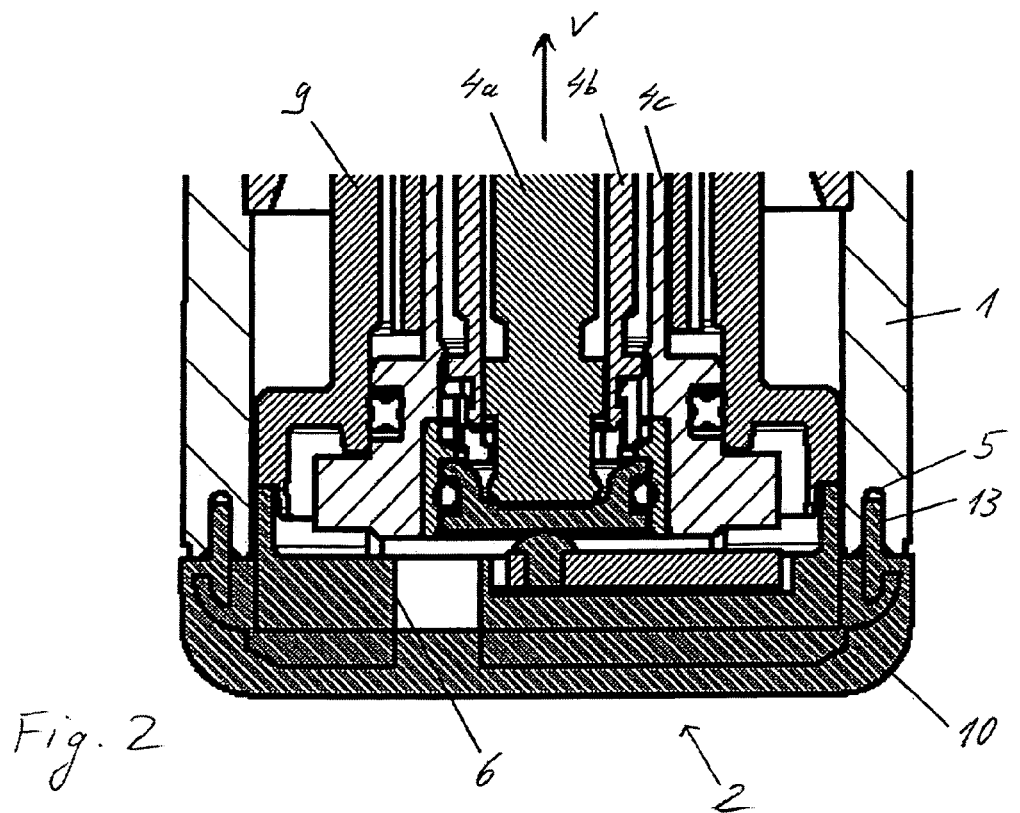
FIG. 2 shows the region where two housing shells of the administering device are joined.

FIG. 2 illustrates the base region of the injection device, in particular the region where the housing shells 1 and 2 are joined, as well as an example of a driver mechanism 4. The driver mechanism 4 comprises a central plunger rod 4a, a central drive member 4b coaxially surrounding the plunger rod 4a and an outer drive member 4c coaxially surrounding the drive member 4b. The drive members 4b and 4c are provided in the form of drive sleeves. The plunger rod 4a and the central drive member 4b engage by means of a thread so that the plunger rod 4a is moved axially in the forward drive direction when the drive member 4b is driven in rotation. The drive members 4b and 4c engage with one another by means of another thread. Together, the plunger rod 4a and the drive members 4b and 4c form a telescopic drive unit for the plunger and, in conjunction with the plunger, the driver mechanism 4. Examples of such telescopic driver mechanisms are described in patent specifications U.S. Pat. No. 09/403,443 and EP 0 991 440 B1, which are included herein by way of reference.

The drive member 4c is axially supported on the support structure 6 in the direction opposite the forward drive direction and, in the embodiment illustrated as an example, the drive member 4c is supported on an axially protruding projection, formed in the central region of the support structure 6. The drive member 4c is supported on the holder 9 in the forward drive direction V and transversely thereto in the radial direction.

The housing shells 1 and 2 are joined to one another by means of a self-sealing connection. The self-sealing connection exists directly between the housing shell 1 and a sealing lip 13 of the seal 10. The sealing lip 13 projects axially from an end face of the seal 10 facing the housing shell 1, i.e. vertically. A seal gap 5 is formed in the housing shell 1 at its terminal end, which opens at the end face of the housing shell 1 facing the end face of housing shell 2. The seal gap 5 projects axially out from its orifice in the end face into the housing shell 1. The seal gap 5 and the sealing lip 13 are each formed so that they extend continuously around a central axis pointing in the forward drive direction V and are in axial alignment with one another. The sealing lip 13 is pressed into the seal gap 5 and establishes a pressing contact with each of the oppositely lying, mutually facing side walls of the seal gap 5. The relevant side walls of the seal gap 5 are parallel with one another and with the forward drive direction V of the driver mechanism 4.

Figure 3:
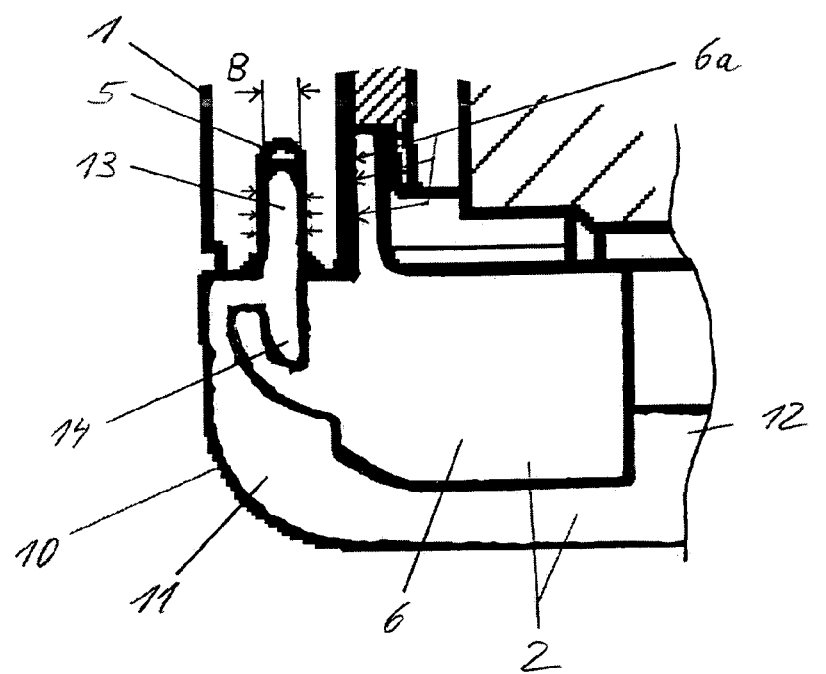
FIG. 3 shows a detail of the joining region.

FIG. 3 is a diagram illustrating a point of the self-sealing connection on a large scale than FIG. 2. The hatching of the support structure 6 and the seal 10 have been omitted solely for the sake of clarity.

The seal gap 5 has a gap width B of a few tenths of a millimeter extending all around it. The manufacturing tolerance of the seal gap 5 with respect to the gap width B is correspondingly small. The manufacturing tolerance is smaller than the standard dimension by at least one order of magnitude, i.e. by at least a factor of 10. If the standard dimension for the gap width B is 0.2 mm, for example, the tolerance is therefore ±0.02 mm, for example. The sealing lip 13 has over size in comparison to the gap width B, so that it is compressed in the narrower seal gap 5 when pressed in and sits in pressing contact with the side walls of the seal gap 5. The pressing pressure bearing on the contact surfaces of the sealing lip 13 is indicated by several small arrows.

The seal 10 is disposed on the external face of the support structure 6 and surrounds the support structure 6, lying tightly against it like a sheath. Consequently, the seal 10 not only forms the sealing lip 13 but also has a shell region 11 which forms a bottom face of the housing shell 2 and hence the housing 1, 2. The shell region 11 is so thick and the material of the seal 10 so soft that the seal 10 also acts as a damping means and anti-slip means on the bottom face of the housing 1, 2. The shape of the seal 10 is akin to that of a flat pan. It extends from the bottom face across its outer peripheral region as far as a top face of the support structure 6 and engages round an outer peripheral edge on the top face of the support structure 6. To obtain an even firmer form fit, it not only engages round the support structure 6 but also engages behind the support structure 6 by means of an anchoring element 14 lying axially opposite the sealing lip 13 and projecting towards the bottom face. Accordingly, the support structure 6 has a recess on its top face, in which the anchoring element 14 is accommodated. In the embodiment illustrated as an example, the recess in the support structure 6 is provided in the form of a peripheral groove and the anchoring element 14 on the seal 10 is provided in the form of a peripheral protuberance similar to the sealing lip 13. Since the seal 10 engages round the support structure 6 and advantageously also engages behind it, a non-positive fit is also obtained between the support structure 6 and the seal 10 in addition to the form fit, because the plastic material from which the seal 10 is made confines the support structure 6 after the injection process. In a central region, the support structure 6 also has an orifice or recess, into which the seal 10 projects by means of a base 12, which completely fills the recess or orifice of the support structure 6. As a result, an additional anchoring is obtained for the support structure 6 in the central region of the seal 10.

The support structure 6 not only acts a support frame for the seal 10 as such, but also as an axial support for the sealing lip 13. To this end, the support structure 6 extends outwards beyond the seal gap 5. The support structure 6 therefore also serves as a stop, by means of which housing shell 2 sits in contact with housing shell 1 in the axial direction in the connected state, so that the axial position of housing shell 2 relative to housing shell 1 is exactly defined when in contact. The relevant end face of the support structure 6 lies opposite the part of the end face of the housing shell 1 which internally adjoins the orifice of the seal gap 5. The part of the end face of housing shell 1 externally adjoining the orifice of the seal gap 5 lies opposite an end face of the seal 10 and is preferably pressed into this end face of the seal 10 with a slight pressing pressure.

In addition to the pressed joint obtained by means of the sealing lip 13, the housing shells 1 and 2 are also non-detachably connected to one another by means of a material join. The material join is obtained by bonding. The region of the material join 6a, which in the embodiment illustrated as an example is a bonded region, extends peripherally along a casing internal face of the housing shell 1 adjoining the end face of the housing shell 1 and a casing external face of the support structure 6 adjoining it in a non-positive fit.

Figure 4:
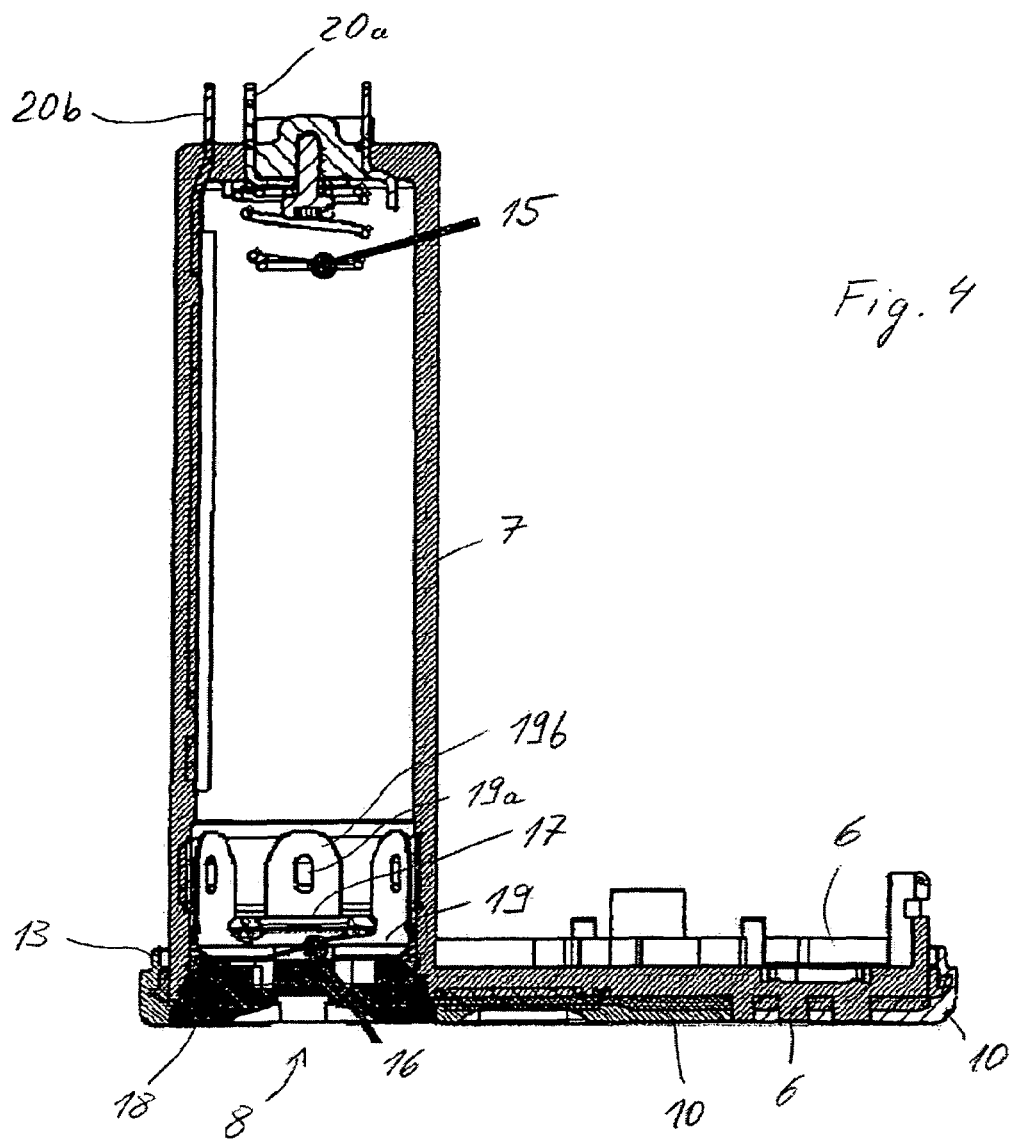
FIG. 4 shows one of the housing shells with a battery compartment.

FIG. 4 is a diagram in section illustrating the compartment 7 of a device for injecting or infusing a product, in which a power source, e.g. a cylindrical battery, can be inserted. The compartment 7 is manufactured in a single piece with the bottom part of the device, e.g. during the injection moulding process. It its bottom face, the compartment 7 has an access opening 8, by means of which the power source can be inserted in the compartment and removed from the compartment. This option is provided because the device may be designed for a longer service life than the power source, which will then have to be replaced whenever necessary. The shape of the compartment 7 for the power source is such that the compartment 7 affords a reliable lateral guiding action for the power source, making it easy to insert the power source.

The access opening 8 can be closed by means of a cover 18. This cover 18 is designed to close off the compartment 7 rendering it watertight because penetration of the compartment by moisture can cause the power source to short-circuit. In order to obtain a high quality seal, the cover 18 is provided in the form of a screw-on cap and also has a sealing ring 26, which is pressed against an internal wall of the compartment 7 when the cap 18 is screwed on.

Disposed at the top end of the compartment 7 is a first contact 15, against which one terminal of the power source can be pushed. The contact is provided in the form of a contact spring 15, which means that it can be elastically compressed when biased by the power source in its insertion direction and spring back into its initial position when no longer biased. The contact spring 15 itself may form an electric down conductor or is connected to a down conductor 20a. The power source is connected to a consumer, e.g. a driver mechanism, by means of this down conductor. In order to establish a connection with the consumer, which as a rule lies outside the compartment 7, the down conductor 20a is run through the external wall of the compartment 7 or is embedded in it during moulding or inserted during the process of injection moulding the compartment 7, in such a way that a terminal piece of the down conductor 20a stands proud of the outer wall of the compartment 7, enabling a connection to a consumer to be plugged in, for example. The first contact spring 15 together with its holder may likewise be embedded in the wall of the compartment 7 during moulding. It could just as easily be secured in the compartment 7 by means of a screw, adhesive, by welding or by similar means. It would also be conceivable for the first contact spring 15 to be made as a single component together with the down conductor, in which case it forms the cover or a part of the cover of the compartment 7 and is inserted in the body of the compartment 7, e.g. bonded.

Likewise disposed on the compartment 7, standing proud of the surface, is another down conductor 20b, which is connected to a second contact spring 16. Like the first contact spring 15, this second contact spring 16 may lie in the compartment 7. By preference, the second contact spring 16 lies in the compartment 7 opposite the first contact spring 15, i.e. the mid-points of the two contact surfaces of the contact springs 15, 16 lie essentially on an axis, e.g. the longitudinal axis of the compartment 7 and extend essentially parallel with one another. The directions in which the first contact spring 15 and the second contact spring 16 can be biased are therefore opposite one another. The spring path of the two contact springs 15, 16 is therefore essentially the same. It is particularly preferable if the second contact spring 16 is secured to the cover 18, as is the case in the embodiment illustrated as an example.

The clearance distance between the contact surface of the first contact spring 15 and the contact surface of the second contact spring 16 is shorter than the length (meaning the distance between the foremost tip of the terminal and the foremost tip of the opposite terminal) of the power source which can be positioned between the contact surfaces. By preference, it is smaller than the length of the power source plus the spring path of one of the contact springs 15, 16. When the power source is biased in the longitudinal direction, this will ensure a reliable contact between the terminals of the power source at all times, even if the power source has a moment of inertia which is different from that of the device or parts of it, due to its relatively high specific weight.

In order to connect the second contact spring 16 via the down conductor 29b to the consumer, a tape of conductive material is attached to a major part of the length of the compartment 7, on or in its internal wall, in the embodiment illustrated as an example here, and is connected to a ring of likewise conductive material provided in the peripheral direction in the bottom region of the compartment 7. When the cap is screwed on, this ring is in contact with indentations 19a of a crown-shaped connecting element 19, which is made from conductive material and is mounted on the cap 19. This connecting element is in turn connected to the second contact spring 16 so that when the power source is inserted, power can be transmitted from the second contact spring 16 via the connecting element 19 and the down conductor 20b to the consumer.

The down conductor 20b need not necessarily be provided in the form of a tape of conductive material, as a wire, with or without insulating sheath, a thin strip or any other connecting geometry would also fall within the scope of this invention. Similarly, the down conductor need not necessarily run through the compartment 7 and instead, a run could be moulded entirely in the wall of the compartment 7 or a run along the external wall of the compartments 7 would also be conceivable. It is merely necessary to ensure that the entire down conductor 20b is disposed inside the sealed housing of the device and a reliable connection to a consumer can be established. Equally, the ring disposed in the peripheral direction mentioned above need not necessarily be a closed ring. As long as it is guaranteed that the connecting element 19, which will be described in more detail below, can reliably establish a contact with the down conductor 20b when the cap 18 is fitted, it may be provided in the form of a part-ring, the extension of the tape itself or a dot-shaped contact point or any other shape of contact surface. In order to establish the requisite contact between the connecting element 19 and down conductor 20b reliably, the last part of the down conductor 20b may also be provided in the form of an increasing material thickness or may project into the compartment 7 due to the shape imparted to the internal wall of the compartment 7 in the region of the connecting element 19.

Figure 5:
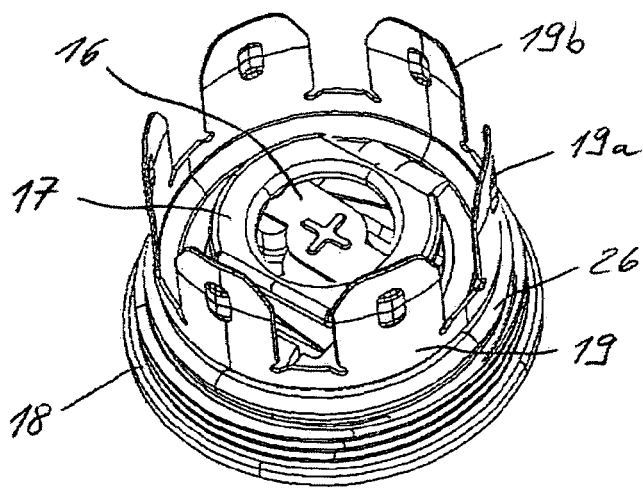
FIG. 5 shows a contact spring integrated in a cover of the battery compartment.

The above-mentioned cap 18 is illustrated in detail in FIG. 5. It essentially consists of a base body with an external thread. This thread fits exactly in the internal thread formed in the access opening 8 of the compartment 7. In the screwed-on state, the cap 18 closes off the compartment 7, and preferably closes it off so that it is watertight. The base body has a side, which is not visible here, which forms the external face of the device in the screwed-on state and may have a locating feature for stowing a cap tool to enable the cap 18 to be firmly pulled on. Attached to the oppositely lying side of the base body, i.e. the side which lies in the interior of the compartment 7 when the cap 18 is screwed on, is the above-mentioned connecting part 19. It may be attached by means of a screw or rivet connection, a bonded or welded connection, a clamp or some other mechanical connection or any other type of connection that will guarantee a reliable connection of the connecting element 19 to the cap 18.

A sealing ring 26 may be inserted between the cap 18 and the connecting element 19 to provide additional sealing. This sealing ring 26 is squashed in the compartment 7 when the cap 19 is firmly screwed on and thus improves the sealing action of the screw connection.

In the embodiment illustrated as an example here, the connecting element 19 is crown-shaped, i.e. several extensions 19b standing vertically proud of the base body are disposed in a circle about the mid-axis of the cap 18. The extensions 19b are connected to one another in the region of the connection with the cap 18 and are also spaced uniformly apart. The extensions may have a simple rectangular shape, with oblique ends, as is the case in the embodiment illustrated as an example, or may be semi-circular, for example. At their top part, i.e. remote from the cap 18, they may have indentations 19a, which are formed by indenting the material of the connecting element 19, for example. The diameter of the circle formed by the extensions 19b is large enough for the power source to be engaged by the extensions 19b in this region.

Disposed in the interior of the crown formed by the connecting element 19 is the second contact spring 16. As with the first contact spring 15, it may be provided in the form of a leaf spring, coil spring, helical spring or bending spring. It stands proud of the cap 18 in the direction towards the interior of the compartment 7 and is able to spring inwards in the opposite direction, i.e. against the cap 18. The second contact spring 16 is conductingly connected to the connecting element 19. This can be achieved using an appropriate connection between the second contact spring 16 and connecting element 19, e.g. a soldered connection, although it would also be conceivable for the connecting element 19 and the contact spring 16 to be made as a single part, in which case it may be made from a thin metal sheet, for example, by an appropriate punching and forming process.

As described above, the power source is connected to the down conductor 20b via the second contact spring 16 and the connecting element 19. If, as is the case in the embodiment illustrated as an example here, the contact is established between the connecting part 19 or its extensions 19b and a ring-shaped metal tape of the down conductor 20b, it may be of advantage to bias the extensions 19b with a radial pre-tensioning force, preferably a pre-tensioning force that is directed radially outwards. This pre-tensioning, either alone or in conjunction with the power source accommodated in the crown formed by the extensions 19b, ensures or ensure a reliable contact.

Instead of the crown illustrated, the connecting element may have only one extension 19b or any number of extensions 19b. If a circle of tape in the interior of the compartment 7 is used as the counter-contact, it will still be possible to establish a reliable contact with only one extension 19b. However, the contact of the down conductor 20b could also extend over only a part of the periphery of the internal wall of the compartment 7 or could be provided in the form of a tape or strip. In the latter case, a reliable contact can still be guaranteed if the connecting element 19 is provided in the form of a closed circle. The decisive factor is that when the cap 18 is firmly screwed on, a contact always exists between the connecting element 19 and the down conductor 20b, by means of which power can be transmitted to a consumer.

In order to prevent failure or incorrect functioning of the device due to incorrect positioning of the power source in the compartment 7, a mispoling protector 17 may be provided. This mispoling protector 17 is made from a non-conducting material and is applied, e.g. bonded, directly to one of the contact springs 15, 16. The mispoling protector may basically be of any shape, but preferably has an annular shape or the shape of a flat, circular disc. This being the case, the thickness of the ring or circular disc is big enough for the projecting opposite terminal, in the case of a battery for example, to project through the hole in the middle of the ring or disc up to the second contact spring 16. If the battery is inserted incorrectly, the mispoling protector 17 must reliably prevent contact between the contact spring 16 and the flat terminal.

Figure 6:
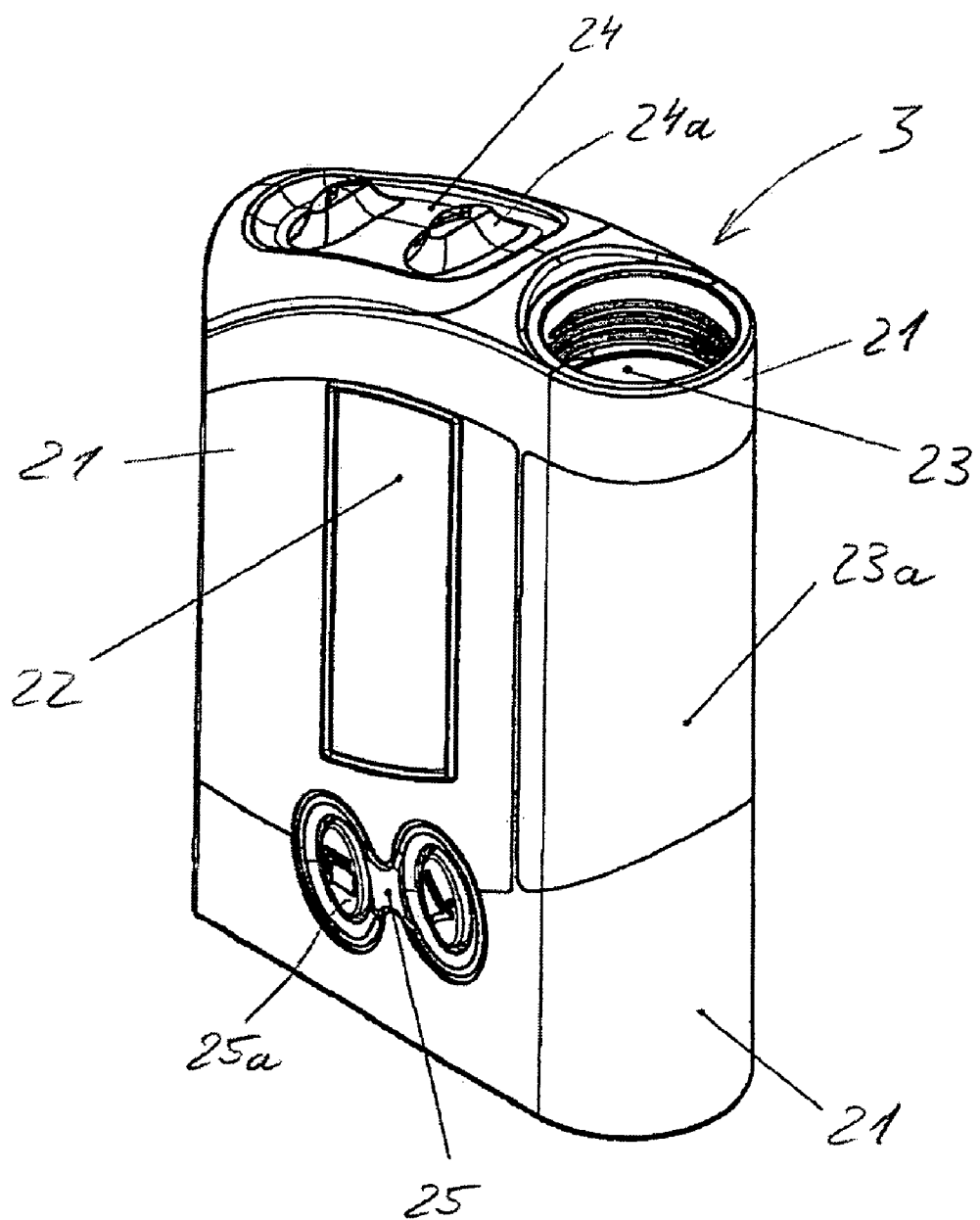
FIG. 6 is a perspective view of the other of the housing shells.

FIG. 6 illustrates the first housing shell 1 in a state immediately after production before the infusion device is assembled. Housing shell 1 forms the side walls and the major part of an upper terminal wall of the housing 1, 2. The shell structure 21 is oval in cross-section with two parallel side walls and two cylindrical, in the embodiment illustrated as an example circular cylindrical, side walls connecting the parallel side walls. The oval hollow cross-section is completely open at the bottom face, where it is closed off by the second housing shell 2 when the infusion device is in the assembled state, as described above. In addition to the open bottom face, the housing shell 1 has only one other opening, namely an opening of the receiver 3 remote from the bottom face. The product container can be inserted in the receiver 3 through the opening. The opening can be closed by means of a screw cap and O-sealing ring, rendering it watertight. The housing shell 1 is watertight with the exception of the two openings.

Insofar as the housing shell 1 forms the external wall of the housing 1, 2, it comprises a shell structure 21, two transparent wall regions 22 and 23a and two flexible wall regions 24 and 25. The wall region 22 is a display window. The wall region 23a forms a larger part of the external wall of the receiver 3 and the wall regions 24 and 25 screen two control fields, each with two control elements. The control elements are push buttons. The wall regions 24 and 25 each have an indentation for each control element, respectively an indentation 24a and 25a. The shape of the indentations 24a and 25a is adapted to the shape of the respective control element. A three-dimensional structure is imparted to the wall regions 24 and 25 as a result of the indentations 24a and 25a, which matches the structure of the respective control field. The control elements behind the wall region 25 are used as a means of controlling a display, for example for retrieving specific information. The control elements behind the wall region 24 are used for controlling the infusion device, for example for selecting a specific bolus. The wall regions 24 and 25 are so flexible that they enable the control elements to be operated without any difficulty.

The shell structure 21 forms a type of skeleton for the housing shell 1. It is made from a plastic material, which is solid and hard enough to provide a dimensionally stable case in spite of having only a slim wall thickness in the range of tenths of a millimeter, which protects the components accommodated in the housing shell 1 from the mechanical stress which can be expected during operation.

The plastic material of the shell structure 21 may be impermeable to light. The wall regions 22 and 23a, on the other hand, are made from a transparent plastic material to enable the display to be read and to ensure that the level control of the product container is visible.

The wall regions 22, 23a, 24 and 25 fill the openings of the shell structure 21. The wall regions 22 to 25 are intrinsically watertight and are connected to the shell structure 21 along the edge of the respective opening of the shell structure 21 around the periphery in a continuous watertight fit.

The housing shell 1 is made by a multi-component injection moulding process. For moulding purposes, the injection mould used has a cavity matching the shape of the housing shell 1, which is filled with moulding material. The wall regions 22 and 23 are also formed by injection moulding before the shell structure 21 is moulded, and the wall region 22 is made as a flat thin disc. The wall region 23a forms a circular tube, which is entirely made from the transparent plastic material and not only forms the transparent wall region 23a of the housing external wall but also forms the side wall of the receiver 3 peripherally.

To make the housing shell 1 by the injection moulding process, the wall region 22 and the tube 23 are placed in the injection mould. To make the shell structure 21 by the injection moulding process, fillers are also placed in the injection mould in place of the wall regions 24 and 25, each of which has the same shape as the opening to be formed in the shell structure 21. Once the fillers and the insert parts 22 and 23 have been positioned, the injection mould is closed and the material of the shell structure 21 is injected in. The plastic material of the shell structure 21 is injected around the insert part 22 along its side edge. Around the insert part 23, the injection takes place on both of its end faces across an arcuate region in each case. The plastic material of the shell structure 21 also adjoins the external face of the insert part 23 in two longitudinal strips and is connected to this external face along the two strips, rendering it watertight.

An injection then takes place in the same manner around the wall regions 22 and 23a, rendering them watertight, and once the plastic material of the shell structure 21 has cured, the injection mould is opened and the fillers removed. The injection mould is then closed again. In a final step of the injection moulding process, the elastomeric plastic material is injected through nozzles that were previously closed into the cavities in the injection mould produced by the fillers, where it is injected onto the shell structure 21. As a result of the latter injection, a watertight connection is produced, extending continuously along the edge of the respective opening of the shell structure 21. The flexible wall regions 24 and 25 are connected to the respective opening edge of the shell structure 21 in a watertight fit along their outer edge due to a combination of the form fit and the material join. The watertight connection of the transparent wall regions 22 and 23a to the shell structure 21 is also essentially based on a material join and form fit between the two plastic materials.

In a preferred variant of the method, the housing shell 2 is produced entirely with one injection mould, with the exception of the insert parts 22 and 23, which are produced beforehand in a separate injection mould or are each produced in a separate injection mould. Once the pre-moulded insert parts 22 and 23 have been placed in the injection mould for making the housing shell 2, the injection mould is closed and the second plastic material is injected around the insert parts 22 and 23. The injection mould then opens and the core of the injection mould together with the shell structure 21 and the insert parts 22 and 23 rotates into a second cavity in the same mould. Before the injection mould closes again, the insert parts 22 and 23 for the next housing shell 2 are placed in the first cavity, which is now free again. Once the mould has closed, the second plastic material is injected around the insert parts 22 and 23 in the first cavity again. In the second cavity, the soft components 24 and 25, i.e. the elastic wall regions, are simultaneously injected. Once the injection mould has opened and the finished housing shell 2 has been ejected from the first cavity and insert parts 22 and 23 have been placed in the first cavity again, the "carousel" starts again.

REFERENCE NUMBERS

1 First housing shell
2 Second housing shell
3 Receiver
4 Conveying mechanism
4a Plunger rod
4b Drive member
4c Drive member
5 Seal gap
6 Support structure
6a Region of material join
6b Raised area
7 Battery compartment 8 Access opening
9 Holder
10 Seal
11 Shell region
12 Base
13 Sealing lip
14 Anchoring element
15 Contact spring
16 Contact spring
17 Mispoling protector
18 Cap
19 Connecting element
19a Projection, indentation
19b Extension
20a Down conductor
20b Down conductor
21 Shell structure
22 Insert part, transparent wall region
23 Insert part
23a Transparent wall region
24 Flexible wall region
24a Indentation
25 Flexible wall region
25a Indentation
26 Sealing ring
B Gap width
V Forward drive direction

The invention claimed is:

1. An administering device for infusing or injecting a product, comprising
 a housing with a receiver for the product;
 a compartment for a power source in order to supply a conveying mechanism with electrical energy;
 a first contact spring which is disposed in the compartment and establishes an electrically conductive contact for a first terminal of the power source via a spring force when the power source is disposed in the compartment; and
a second contact spring for establishing an electrically conducting contact for a second-terminal of the power source via a spring force;
 wherein either the first contact spring or the second contact spring comprises a structure which prevents current from flowing if the power source is inserted in the compartment incorrectly, wherein the structure comprises a non-conducting material in the form of a ring having a thickness which is shorter than the length of a protrusion extending from one of the terminals of the power source.

2. The administering device as claimed in claim 1, wherein the first contact spring and the second contact spring are disposed in the compartment.

3. The administering device of claim 1, wherein the structure is directly affixed to the second contact spring.

4. The administering device of claim 1, wherein the contact springs comprise compression springs between which the power source can be disposed.

5. The administering device of claim 1, wherein force vectors of the first and the second contact spring point in opposite directions when the compartment is closed and extend essentially parallel with the longitudinal axis of the compartment, and the first contact spring is in springing contact with the terminal of the power source and the second contact spring is in contact with its opposite terminal.

6. The administering device of claim 1, wherein the first contact spring and the second contact spring are each connected to a respective down conductor which connects the power source to the conveying mechanism.

7. The administering device of claim 1, wherein the compartment comprises a cover for closing an access opening of the compartment on the housing.

8. The administering device of claim 7, wherein the cover is a screw-on cap.

9. The administering device of claim 7, wherein the cover comprises a connecting element on an internal face.

10. The administering device of claim 9, wherein a sealing ring is inserted in a connecting region between the cover and the connecting element.

11. The administering device of claim 9, wherein the connecting element comprises at least one extension extending in an axial direction of the compartment which projects from the cover into the compartment.

12. The administering device of claim 11, wherein the extension is radially pre-tensioned.

13. The administering device of claim 11, wherein the extension comprises at least one radial projection in contact with an electrical down conductor extending in an interior of the compartment in a peripheral direction when the cover closes off the access opening.

14. The administering device of claim 7, wherein the second contact spring is disposed on the cover.

15. The administering device of claim 14, wherein the second contact spring is a leaf spring.

16. The administering device of claim 14, wherein the second contact spring is conductively connected to the connecting element.

17. The administering device of claim 16, wherein the connecting element and the contact spring are formed as a single piece.

18. An administering device for infusing or injecting a product, comprising:
 a housing with a receiver for the product;
 a compartment for a power source in order to supply a conveying mechanism with electrical energy;
 a first contact spring which is disposed in the compartment and establishes an electrically conductive contact for a first terminal of the power source via a spring force when the power source is disposed in the compartment; and
 a second contact spring for establishing an electrically conducting contact for a second terminal of the power source via a spring force;
 wherein either the first contact spring or the second contact spring comprises a structure which prevents current from flowing if the power source is inserted in the compartment incorrectly, wherein the structure comprises a non-conducting material having a thickness which is shorter than the length of a protrusion extending from one of the terminals of the power source.

* * * * *

UNITED STATES PATENT AND TRADEMARK OFFICE
CERTIFICATE OF CORRECTION

PATENT NO. : 7,655,351 B2 Page 1 of 1
APPLICATION NO. : 11/345640
DATED : February 2, 2010
INVENTOR(S) : Philip Etter et al.

It is certified that error appears in the above-identified patent and that said Letters Patent is hereby corrected as shown below:

SPECIFICATION

| Column | Line | PTO | Should Read |
|---|---|---|---|
| 4 | 21 | "U.S. Pat. No. 09/409,443" | -- U.S. Pat. Appl. No. 09/409,443 -- |

Signed and Sealed this

Thirtieth Day of March, 2010

David J. Kappos
*Director of the United States Patent and Trademark Office*